United States Patent
Giger et al.

(10) Patent No.: US 7,184,582 B2
(45) Date of Patent: Feb. 27, 2007

(54) METHOD, SYSTEM AND COMPUTER READABLE MEDIUM FOR AN INTELLIGENT SEARCH WORKSTATION FOR COMPUTER ASSISTED INTERPRETATION OF MEDICAL IMAGES

(75) Inventors: Maryellen L. Giger, Elmhurst, IL (US); Carl J. Vyborny, Riverside, IL (US); Zhimin Huo, Chicago, IL (US); Li Lan, Naperville, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 10/793,799

(22) Filed: Mar. 8, 2004

(65) Prior Publication Data

US 2004/0247166 A1 Dec. 9, 2004

Related U.S. Application Data

(63) Continuation of application No. 09/773,636, filed on Feb. 2, 2001, now Pat. No. 6,901,156.

(60) Provisional application No. 60/207,401, filed on May 30, 2000, provisional application No. 60/180,162, filed on Feb. 4, 2000.

(51) Int. Cl.
*G06K 9/00* (2006.01)
(52) U.S. Cl. .................... 382/128; 382/168; 378/28
(58) Field of Classification Search ........ 382/128–133, 382/156, 162, 165, 168, 169, 199, 203, 219, 382/237, 254, 266, 274, 285, 316, 321; 250/455; 600/408, 443, 425; 356/39; 377/10; 378/21, 378/28, 37; 345/418, 604; 348/77, 180; 707/104.1
See application file for complete search history.

(56) References Cited

U.S. PATENT DOCUMENTS 4,907,156 A 3/1990 Doi et al.

(Continued)

FOREIGN PATENT DOCUMENTS

| WO | WO 99/30264 | 6/1999 |
|----|-------------|--------|
| WO | WO 00/05677 | 2/2000 |

OTHER PUBLICATIONS

Katherine P. Andriole, et al. "Finding-Specific Display Presets for Computed Radiography Soft-Copy Reading"; Journal of Digital Imaging, vol. 12, No. 2, Suppl. 1, May 1999, pp. 3-5.

(Continued)

*Primary Examiner*—Matthew C. Bella
*Assistant Examiner*—Seyed Azarian
(74) *Attorney, Agent, or Firm*—Oblon, Spivak, McClelland, Maier & Neustadt, P.C.

(57) ABSTRACT

A method, system and computer readable medium for an intelligent search display into which an automated computerized image analysis has been incorporated. Upon viewing an unknown mammographic case, the display shows both the computer classification output as well as images of lesions with known diagnoses (e.g., malignant vs. benign) and similar computer-extracted features. The similarity index used in the search can be chosen by the radiologist to be based on a single feature, multiple features, or on the computer estimate of the likelihood of malignancy. Specifically the system includes the calculation of features of images in a known database, calculation of features of an unknown case, calculation of a similarity index, display of the known cases along the probability distribution curves at which the unknown case exists. Techniques include novel developments and implementations of computer-extracted features for similarity calculation and novel methods for the display of the unknown case amongst known cases with and without the computer-determined diagnoses.

15 Claims, 8 Drawing Sheets

U.S. PATENT DOCUMENTS

| | | |
|---|---|---|
| 5,133,020 A | 7/1992 | Giger et al. |
| 5,260,871 A | 11/1993 | Goldberg |
| 5,373,452 A | 12/1994 | Guha |
| 5,452,367 A * | 9/1995 | Bick et al. ................. 382/128 |
| 5,537,485 A * | 7/1996 | Nishikawa et al. ......... 382/130 |
| 5,638,458 A | 6/1997 | Giger et al. |
| 5,657,362 A | 8/1997 | Giger et al. |
| 5,666,434 A | 9/1997 | Nishikawa et al. |
| 5,754,676 A | 5/1998 | Komiya et al. |
| 5,784,162 A | 7/1998 | Cabib et al. |
| 5,799,100 A | 8/1998 | Clarke et al. |
| 5,832,103 A | 11/1998 | Giger et al. |
| 5,881,124 A | 3/1999 | Giger et al. |
| 5,970,164 A | 10/1999 | Bamberger et al. |
| 5,974,165 A | 10/1999 | Giger et al. |
| 5,982,917 A * | 11/1999 | Clarke et al. ............... 382/132 |
| 5,984,870 A * | 11/1999 | Giger et al. ................. 600/443 |
| 6,058,322 A | 5/2000 | Nishikawa et al. |
| 6,078,680 A | 6/2000 | Yoshida et al. |
| 6,112,112 A | 8/2000 | Gilhuijs et al. |
| 6,138,045 A * | 10/2000 | Kupinski et al. ........... 600/425 |
| 6,141,437 A | 10/2000 | Xu et al. |
| 6,185,320 B1 * | 2/2001 | Bick et al. ................. 382/132 |
| 6,282,305 B1 | 8/2001 | Huo et al. |
| 6,282,307 B1 | 8/2001 | Armato, III et al. |
| 6,317,617 B1 | 11/2001 | Gilhuijs et al. |
| 6,335,980 B1 | 1/2002 | Armato, III et al. |
| 6,470,092 B1 | 10/2002 | Li et al. |
| 6,630,937 B2 * | 10/2003 | Kallergi et al. ............. 345/619 |
| 6,941,323 B1 * | 9/2005 | Galperin .................. 707/104.1 |

OTHER PUBLICATIONS

Andriole, Katherine P., Gould, Robert G., and Webb, W. Richard, "Finding-Specific Display Presets for Computed Radiography Soft-Copy Reading", Supplement to The Official Journal of The Society for Computer Applications in Radiology, SCAR 99, Proceedings of the 16th Symposium for Computer Applications in Radiology, "PACS: Performance Improvement in Radiology", Houston, TX, May 6-9, 1999, vol. 12, No. 2, Suppl. 1, May 1999.

Zhimin Huo et al., "Effect of Dominant Features on Neural Network Performing in the Classification of Mammographic Lesions", *Phys. Med. Bio.*, 44, c1999, pp. 2579-2595.

Zhimin Huo et al., "Automated Computerized Classification of Malignant and Benign Masses on Digitized Mammograms", *Acad Radiol*, vol. 5, No. 3, Mar. 1998, pp. 155-168.

Zhimin Huo et al., "Analysis of Spiculation in the Computerized Classification of Mammographic Masses", *Medical Physics*, vol. 22, No. 10, Oct. 1995, pp. 1569-1579.

J. Sklansky et al., "A Visualized Mammographic Database in Computer-Aided Diagnosis", *Computer-Aided Diagnosis in Medical Imaging*, c1999, pp. 215-220.

U.S. Appl. No. 09/759,333, filed Jan. 16, 2001, Armato et al.
U.S. Appl. No. 09/760,854, filed Jan. 17, 2001, Armato et al.
U.S. Appl. No. 09/990,377, filed Nov. 23, 2001, Li et al.
U.S. Appl. No. 10/793,799, filed Mar. 08, 2004, Giger et al.
U.S. Appl. No. 10/777,041, filed Feb. 13, 2004, Giger et al.
U.S. Appl. No. 10/793,799, filed Mar. 8, 2004, Giger et al.

* cited by examiner

METHOD, SYSTEM AND COMPUTER READABLE MEDIUM FOR AN INTELLIGENT SEARCH WORKSTATION FOR COMPUTER ASSISTED INTERPRETATION OF MEDICAL IMAGES

CROSS-REFERENCE TO RELATED APPLICATIONS

This application claims priority under 35 U.S.C. § 119(e) to U.S. provisional patent applications Ser. No. 60/180,162, filed on Feb. 4, 2000 and Ser. No. 60/207,401, filed on May 30, 2000 and also priority under 35 U.S.C. § 120 to U.S. patent application Ser. No. 09/773,636, filed on Feb. 2, 2001, now U.S. Pat. No. 6,901,156, each of which is incorporated by reference herein.

BACKGROUND OF THE INVENTION

1. Field of the Invention

The invention relates generally to the field of computer-aided diagnosis and image display workstations. It describes a method, system and computer readable medium that employs an intelligent search workstation for the computer assisted interpretation of medical images. Upon viewing an unknown medical case, the workstation shows both computer analysis output as well as images of cases with known diagnoses (e.g., malignant vs. benign) and similar computer-extracted features. The similarity index used in the search can be chosen by the radiologist to be based on a single feature, multiple features, or on the computer estimate of the likelihood of disease (such as malignancy in breast cancer). The present invention also generally relates to computerized techniques for automated analysis of digital images, for example, as disclosed in one or more of U.S. Pat. Nos. 4,839,807; 4,841,555; 4,851,984; 4,875,165; 4,907,156; 4,918,534; 5,072,384; 5,133,020; 5,150,292; 5,224,177; 5,289,374; 5,319,549; 5,343,390; 5,359,513; 5,452,367; 5,463,548; 5,491,627; 5,537,485; 5,598,481; 5,622,171; 5,638,458; 5,657,362; 5,666,434; 5,673,332; 5,668,888; 5,732,697; 5,740,268; 5,790,690; 5,832,103; 5,873,824; 5,881,124; 5,931,780; 5,974,165; 5,982,915; 5,984,870; 5,987,345; and 6,011,862; as well as U.S. patent application Ser. Nos. 08/173,935; 08/398,307 (PCT Publication WO 96/27846); 08/536,149; 08/562,087; 08/900,188; 08/900,189; 08/900,191; 08/900,361; 08/979,623; 08/979,639; 08/982,282; 09/027,468; 09/027,685; 09/028,518; 09/053,798; 09/092,004; 09/121,719; 09/131,162; 09/141,535; 09/156,413; 09/298,852; and 09/471,088; PCT patent applications PCT/US99/24007; and PCT/US99/25998; and U.S. provisional patent application 60/160,790; filed on Jan. 18, 2000, all of which are incorporated herein by reference.

The present invention includes use of various technologies referenced and described in the above-noted U.S. Patents and Applications, as well as described in the references identified in the appended LIST OF REFERENCES by the author(s) and year of publication and cross-referenced throughout the specification by numerals in brackets corresponding to the respective references, the entire contents of which, including the related patents and applications listed above and references listed in the LIST OF REFERENCES, are incorporated herein by reference.

2. Discussion of the Background

Breast cancer is a leading cause of death in women, causing an estimated 46,000 deaths per year. Mammography is the most effective method for the early detection of breast cancer, and it has been shown that periodic screening of asymptomatic women does reduce mortality. Many breast cancers are detected and referred for surgical biopsy on the basis of a radiographically detected mass lesion or cluster of microcalcifications. Although general rules for the differentiation between benign and malignant mammographically identified breast lesions exist, considerable misclassification of lesions occurs with the current methods. On average, less than 30% of masses referred for surgical breast biopsy are actually malignant.

Accordingly, due shortcomings in the above-noted methods, an improved method, system and computer readable medium for the computer assisted interpretation of medical images is desirable.

SUMMARY OF THE INVENTION

Accordingly, an object of this invention is to provide a method, system and computer readable medium that employs an intelligent search workstation for the computer assisted interpretation of medical images.

Another object of the invention is to provide an automated method, system and computer readable medium that employs an intelligent search workstation for the computer assisted interpretation of medical images based on computer-estimated likelihood of a pathological state, e.g., malignancy.

Another object of the invention is to provide a method, system and computer readable medium that employs an intelligent search workstation for the computer assisted interpretation of medical images and outputs to the radiologist/physician output from the computer analysis of the medical images.

These and other objects are achieved according to the invention by providing an improved method, system and computer readable medium for computer assisted interpretation of a medical image, including obtaining image data representative of a medical image; computing at least one feature characteristic of the image data; comparing the computed feature characteristic to corresponding computed feature characteristics derived from images in a known image data set; selecting image data from images of the known image data set having corresponding computed feature characteristics similar to the feature characteristics computed in the computing step; displaying at least one of the selected image data and the obtained image data.

The present invention accordingly includes a computer readable medium storing program instructions by which the method of the invention can be performed when the stored program instructions are appropriately loaded into a computer, and a system for implementing the method of the invention.

The method, system computer readable medium of the intelligent search workstation combines the benefit of computer-aided diagnosis with prior knowledge obtained via confirmed cases. It is expected that the display of known lesions with similar features will aid the radiologist in his/her work-up of a suspect lesion, especially when the radiologist's assessment of the lesion differs from the computer output, for the computerized assessment of tumor extent in magnetic resonance images.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings wherein.

DETAILED DESCRIPTION OF THE PREFERRED EMBODIMENTS

Figure 1:
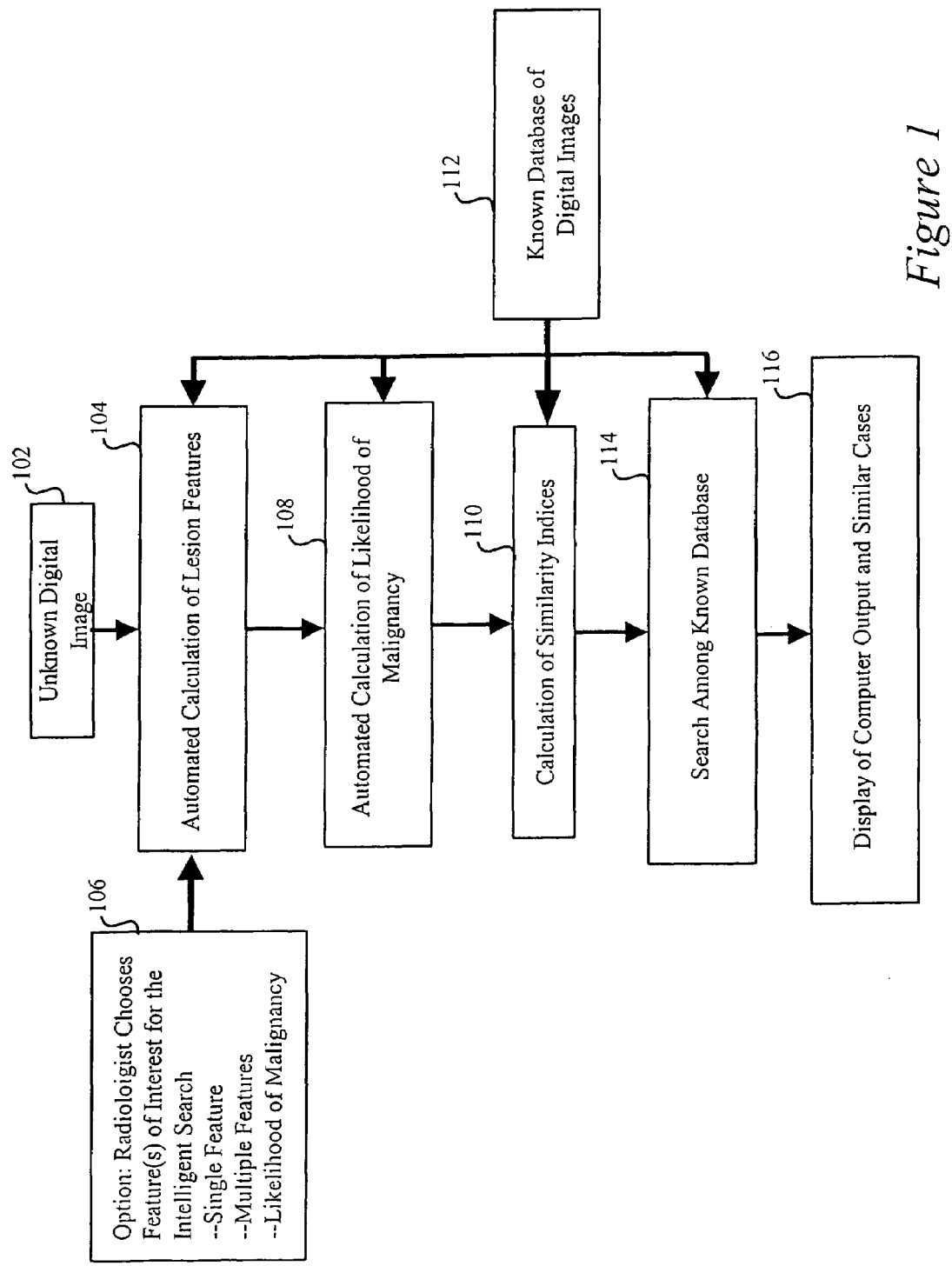
FIG. 1 is a flow chart illustrating the overall scheme for a method that employs an intelligent search workstation for the computer assisted interpretation of medical images.

The inventors are investigating the potential usefulness of computer-aided diagnosis as an aid to radiologists in the characterization and classification of mass lesions in mammography. Observer studies show that such a system can aid in increasing the diagnostic accuracy of radiologists both in terms of sensitivity and specificity. The present mass classification method, system and computer readable medium includes three components: (1) automated segmentation of mass regions, (2) automated feature-extraction, and (3) automated classification [1–3]. The method is initially trained with 95 mammograms containing masses from 65 patients. Features related to the margin, shape, and density of each mass are extracted automatically from the image data and merged into an estimate of the likelihood of malignancy using artificial neural networks (ANNs). These features include a spiculation measure, a radial gradient index, and two density measures. The round-robin performance of the computer in distinguishing between benign and malignant masses is evaluated by receiver operating characteristic (ROC) analysis. The computer classification scheme yielded an $A_z$ value of 0.94, similar to that of an experienced mammographer ($A_z$=0.91) and statistically significantly higher than the average performance of five radiologists with less mammographic experience ($A_z$=0.80). With the database used, the computer scheme achieved, at 100% sensitivity, a positive predictive value of 83%, which is 12% higher than that of the experienced mammographer and 21% higher than that of the average performance of the less experienced mammographers at a p-value of less than 0.001.

The computerized mass classification method is next independently evaluated on a 110-case clinical database consisting of 50 malignant and 60 benign cases. The effects of variations in both case mix and in film digitization technique on the performance of the method are assessed. Categorization of lesions as malignant or benign using the computer achieved an $A_z$ value (area under the ROC curve) of 0.90 on the prior training database (Fuji scanner digitization) in a round-robin evaluation, and $A_z$ values of 0.82 and 0.81 on the independent database for Konica and Lumisys digitization formats, respectively. However, the statistical comparison of these performances fails to show a statistical significant difference between the performance on the training database and that on the independent validation database (p-values>0.10). Thus, the computer-based method for the classification of lesions on mammograms is shown to be robust to variations in case mix and film digitization technique.

The inventors have now developed an intelligent search display into which has been incorporated the computerized mass classification method. Upon viewing an unknown mammographic case, the display shows both the computer classification output as well as images of lesions with known diagnoses (e.g., malignant vs. benign) and similar computer-extracted features. The similarity index used in the search can be chosen by the radiologist to be based on a single feature, multiple features, or on the computer estimate of the likelihood of malignancy.

The output of a computer-aided diagnostic scheme can take a variety of forms such as the estimated likelihood that a lesion is malignant either in terms of probabilities or along a standardized rating scale. This information is then available for use by the radiologist as he or she sees fit when making decisions regarding patient management. An alternative approach is for the computer to display a variety of lesions that have characteristics similar to the one at band and for which the diagnosis is known, thereby providing a visual aid for the radiologist in decision making. Swett et al [4, 5] presented such a method in the Mammo/Icon system which used human input characteristics of the lesion in question. Sklansky et al [6] uses a visual neural network and displays the feature plot of the known database with the unknown case indicated. The intelligent workstation according to the present invention is unique in that it recalls lesions in the known database based either on a single feature, multiple features, or computer-estimate of the likelihood of malignancy. In addition, instead of just displaying typical malignant and benign cases that are similar, the computer display shows relative similarity of the malignant and benign known cases by use of a color-coding of the similar lesions. Basically, the probability distributions of the malignant and benign cases in the known database are shown by images along with the "location" of the unknown case relative to the two distributions.

The intelligent search workstation combines the benefit of computer-aided diagnosis with prior knowledge obtained via confirmed cases. It is expected that the display of known lesions with similar features will aid the radiologist in his/her workup of a suspect lesion, especially when the radiologist's assessment of the lesion differs from the computer output.

Referring now to the drawings, wherein like reference numerals designate identical or corresponding parts throughout the several views, and more particularly to FIG. 1 thereof, there is illustrated a top level block diagram of the method that employs an intelligent search workstation for the computer assisted interpretation of medical images according to the present invention.

The overall scheme includes an initial acquisition of a set of known medical images that comprise a database, and presentation of the images in digital format. The lesion location in terms of estimated center is input from either a human or computer. The method, system and computer readable medium that employs an intelligent search workstation for the computer assisted interpretation of medical images consists of the following stages: access to a database of known medical images with known/confirmed diagnoses of pathological state (step 112), computer-extraction of features of lesions within the known database (step 104), input method for an unknown case (step 102), computer-extraction of features of lesion of the unknown case (step 104), calculation of likelihood of pathological state (e.g., likelihood of malignancy) for the known and unknown cases (step 108), calculation of similarity indices for the unknown cases relative to each of the known cases (step 110), search among the known database based on the calculated similarity indices (step 114) and presentation of the "similar" cases and/or the computer-estimated features and/or likelihood of pathological state (step 116). A specific example of the system is given for mass lesions in mammographic images in which the computer extracts features (step 104) and estimates the likelihood of malignancy for the known and the unknown cases (step 108), computes the similarity indices for each pair (step 110), and output cases that are similar in terms of individual features, combination of features, and/or computer-estimated likelihood of malignancy (step 116). The radiologist has the option of choosing various features, such as single feature, multiple features, likelihood of malignancy, etc., for the analysis (step 106).

Database

Figure 2:
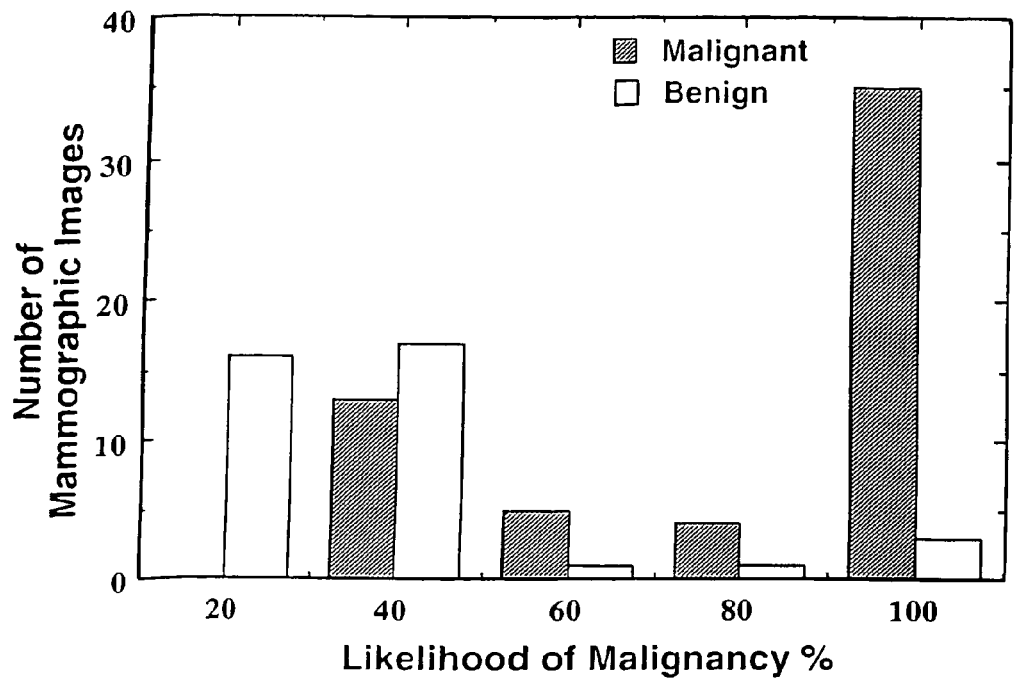
FIG. 2 is a graph illustrating the distribution of cases of mammographic mass lesions in the known database.
Figure 3:
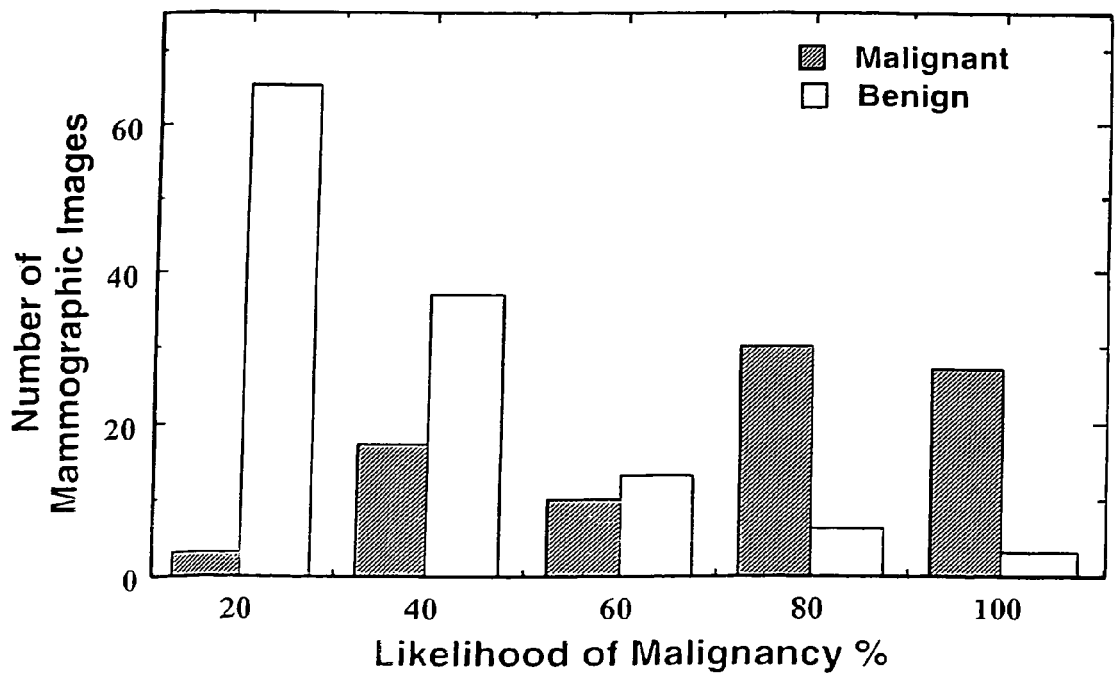
FIG. 3 is a graph illustrating the distribution of tumor pathology in the database used in the demonstration and evaluation of the presented method, system and computer readable medium.

The images used are obtained by mammography followed by film digitization. The database used consists of 95 clinical mammograms (Kodak MinR screen/OM-1 film, Eastman Kodak, Rochester, N.Y.), each containing a mass. Of the ninety five mammographic masses, 38 are benign and 57 are malignant. All but one case is verified by biopsy; the remaining one is deemed benign by long-term follow-up as illustrated in the graph of FIG. 2. The computerized mass classification method is independently evaluated on a 110-case clinical database consisting of 50 malignant and 60 benign cases as illustrated in the graph of FIG. 3.

Automated Classification of Mass Lesions

Figure 4:
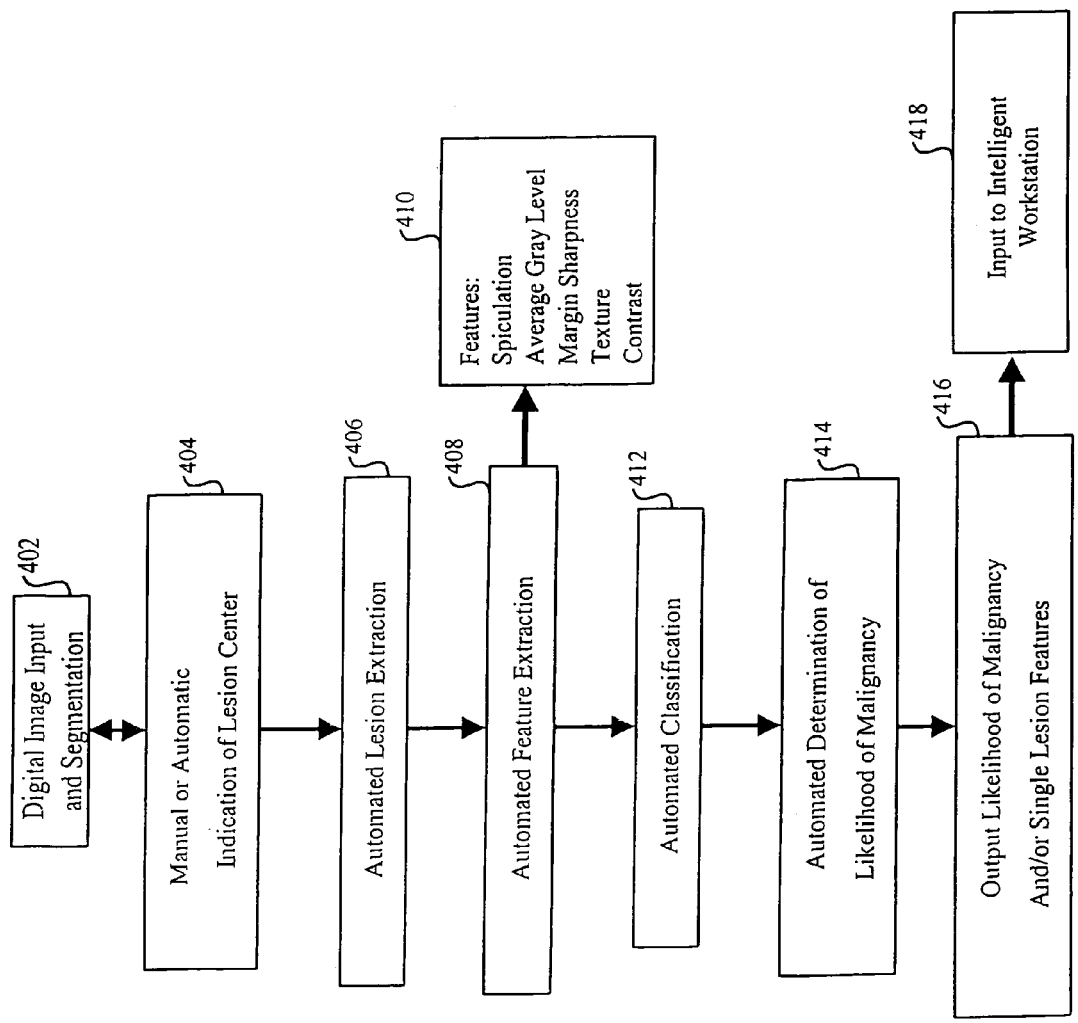
FIG. 4 is a flow chart illustrating the method for computer calculation of the features and estimate of the likelihood of malignancy.

As shown in the flow chart of FIG. 4, the mass classification method includes three components: (1) automated segmentation of mass regions including inputting of digital images (step 402), manual or automatic indication of lesion center (step 404), and automated lesion extraction (step 406), (2) automated feature-extraction (step 408) for predetermined features, such as spiculation, shape, margin sharpness, texture, etc. (step 410), and (3) automated classification (step 412). [1–3]. After automated determination of the likelihood of malignancy is preformed (step 414), the likelihood of malignancy and/or lesion features output (step 416) are input to the intelligent workstation (step 418).

The segmentation (step 402) of a mass from the background parenchyma is accomplished using a multiple-transition-point, gray level region-growing technique. Segmentation begins within a 512×512 pixel region of interest manually or automatically centered about the abnormality in question (step 404). In clinical practice, the location of the mass can be identified either by a radiologist or by a computer-detection scheme and then fed into the classification scheme for an output on the likelihood of malignancy. In order to correct for the nonuniformity of the background distribution and to enhance image contrast for better segmentation of masses, background trend correction and histogram equalization techniques are applied to the 512×512 region of interest.

The margin, shape and density of a mass are three major characteristics used by radiologists in classifying masses. Different characteristics of these features are associated with different levels of probabilities of malignancy. In order to determine the likelihood of malignancy associated with different margin and density characteristics, the inventors developed algorithms that extract (step 408), for example, two features that characterize the margin of a mass (e.g., spiculation and margin sharpness) and three features that characterize the density of a mass (e.g., average gray level, contrast and texture).

Margin characteristics typically are very important discriminants in differentiating between benign and malignant masses. In order to determine the likelihood of malignancy of a mass based on its margin, two major margin characteristics—a spiculation measure and a margin-sharpness measure—are developed. Margin spiculation typically is the most important indicator for malignancy with spiculated lesions having a greater than 90% probability of malignancy. Margin sharpness typically is also very important in determination of the benign vs. malignant nature of a mass—with an ill-defined margin indicating possible malignancy and a well-defined margin indicating likely benignity. Only about 2% of well-defined masses are malignant.

The spiculation measure is obtained from an analysis of radial edge gradients. The spiculation measure evaluates the average angle (degrees) by which the direction of the maximum gradient at each point along the margin of a mass deviates from the radial direction, the direction pointing from the geometric center of the mass to the point on the margin. The actual measure is the full width at half-maximum (FWHM) of the normalized edge-gradient distribution calculated for a neighborhood of the grown region of the mass with respect to the radial direction. This measure is able to quantify the degree of spiculation of a mass primarily because the direction of maximum gradient along the margin of a spiculated mass varies greatly from its radial direction, whereas the direction of the maximum gradient along the margin of a smooth mass is similar to its radial direction.

The spiculation measure achieved a similar level of performance ($A_z=0.88$) to that of the experienced mammographer's spiculation ratings ($A_z=0.85$) in terms of the ability to distinguish between benign and malignant masses based solely on spiculation. [1]

The sharpness of the margin of a mass, for example, can be described as well-defined, partially ill-defined or ill-defined. The average margin sharpness can be quantified by calculating the magnitude of the average gradient along the margin of the mass. A well-defined margin has a large value for the average margin sharpness measure, whereas an ill-defined margin has a small value.

Although the radiographic density of a mass may not be by itself as powerful a predictor in distinguishing between benign and malignant masses as its margin features, taken with these features, density assessment typically can be extremely useful. The evaluation of the density of a mass is of particular importance in diagnosing circumscribed, lobulated, indistinct, or obscured masses that are not spiculated.

In order to assess the density of a mass radiographically, introduced are three density-related measures (e.g., average gray level, contrast, and texture measure) that characterize different aspects of the density of a mass. These measures are similar to those used intuitively by radiologists. Average gray level is obtained by averaging the gray level values of each point within the grown region of a mass. Contrast is the difference between the average gray level of the grown mass and the average gray level of the surrounding fatty areas (e.g., areas with gray level values in the lower 20% of the histogram for the total surrounding area). Texture is defined here as the standard deviation of the average gradient within a mass and it is used to quantify patterns arising from veins, trabeculae, and other structures that may be visible through a low-density mass, but not through a high-density mass. A mass of low radiographic density should have low values of average gray level and contrast, and a high value of the texture measure, whereas a mass of high radiographic density should have high values of average gray level and contrast, and a low value of the texture measure.

Classifier

Three automated classifiers (step 412) are investigated for the task of merging the computer-extracted features (step 408) into an estimate of the likelihood of malignancy (step 414): (1) a rule-based method; (2) an artificial neural network; and (3) a hybrid system (i.e., combination of a one-step rule-based method and an artificial neural network). In determining the likelihood of malignancy (step 414) for the cases that had both the medio-lateral-oblique and cranio-caudal views, the measurements obtained from both views are considered and the one with the higher likelihood of malignancy estimated by the computer (step 414) is used in the evaluation. For example, in these cases, a mass would be classified as malignant if either one of the two views showed suspicious signs, e.g., either one of the FWHM measures from its two views satisfied the cutoff on the FWHM measure.

A rule-based method adopts knowledge from experts into a set of simple rules. Certain criteria for differentiating between benign and malignant masses have been established by expert mammographers. The rules employed in the present approach for spiculation, margin-sharpness and density measures are based on these criteria. A two-step rule-based method is studied for this database. Because of its clinical diagnostic significance, the spiculation measure is applied first in the rule-based method. After the spiculation measure (e.g., FWHM) is applied to identify spiculated masses (e.g., including some irregular masses) and categorized them as malignant first, a second feature is applied to further characterize the masses in the non-spiculated category as previously discussed. In order to investigate the potential discriminant ability of the spiculation measure along with all the possible secondary features, applied separately is each of the remaining four features—the margin-sharpness measure and the three density measures—after the spiculation measure. The threshold of the spiculation measure (e.g., FWHM of 160 degrees) is determined based on the entire database. The thresholds of the other four features are determined based on the remaining database only.

The ANN approach is quite different from the rule-based method. Instead of using prespecified empirical algorithms based on prior knowledge, ANNs are able to learn from examples and therefore can acquire their own knowledge through learning. Also, neural networks are capable of processing large amounts of information simultaneously. Neural networks typically do not, however, provide the user with explanations about their decisions and may not be able to bring pre-existing knowledge into the network. Here employed is a conventional three-layer, feed-forward neural network with a back-propagation algorithm, which has been used in medical imaging and medical decision making. The structure of the neural network, for example, includes four input units (e.g., each of which corresponded to a computer-extracted feature), two hidden units, and one output unit.

To determine the ability of the neural network to generalize from the training cases and make diagnoses for cases that had not been included in the database, employed is a round-robin method—also known as the leave-one-out method. In this method, all but one case is used to train the neural network. The single case that is left out is used to test the neural network. For the cases having both medio-lateral-oblique and cranio-caudal views, both images of the pair are left out in the round-robin training. The higher value of the two from the round-robin test is reported as the estimated likelihood of malignancy. This procedure is repeated for all the cases.

Each classifier has its advantages and limitations. With rule-based methods, one can adopt pre-existing knowledge as rules. However, there are limitations in the availability of knowledge and knowledge translation. Even the experts find it difficult to articulate particular types of "intuitive" knowledge, and the process of translating particular knowledge into rules is limited by this expressive power. ANNs are capable of learning from examples and therefore can acquire their own knowledge. It may be most advantageous to use ANNs when intuitive knowledge cannot be explicitly expressed or is difficult to translate. However, the ANN requires a sufficiently large database to learn effectively. Also, with an ANN there may be uncertainty as to whether the final learning goal is achieved in some situations. To take advantage of both rule-based systems and ANNs in the task of classifying masses, integrated is a rule-based method and an ANN into a hybrid system. In the hybrid system, initially is applied a rule on the spiculation measure since both spiculated and irregular masses are highly suspicious for malignancy, and then is applied an ANN to the remaining masses. Basically, this frees the ANN from having to "learn" the significance of spiculation to the detriment of learning the significance of the other features.

The threshold of the spiculation measure for the hybrid system is the same as the one used in the rule-based method. The ANN applied in the hybrid system is a three-layer, feed-forward neural network with a back-propagation algorithm that has a structure of three input units (e.g., corresponding to the three remaining features used in the ANN method), two hidden units, and one output unit. The same round-robin method is applied to test the generalization ability of this neural network to differentiate between benign and malignant masses in the non-spiculated category.

Evaluation of Automated Classification of Mass Lesions

Figure 5:
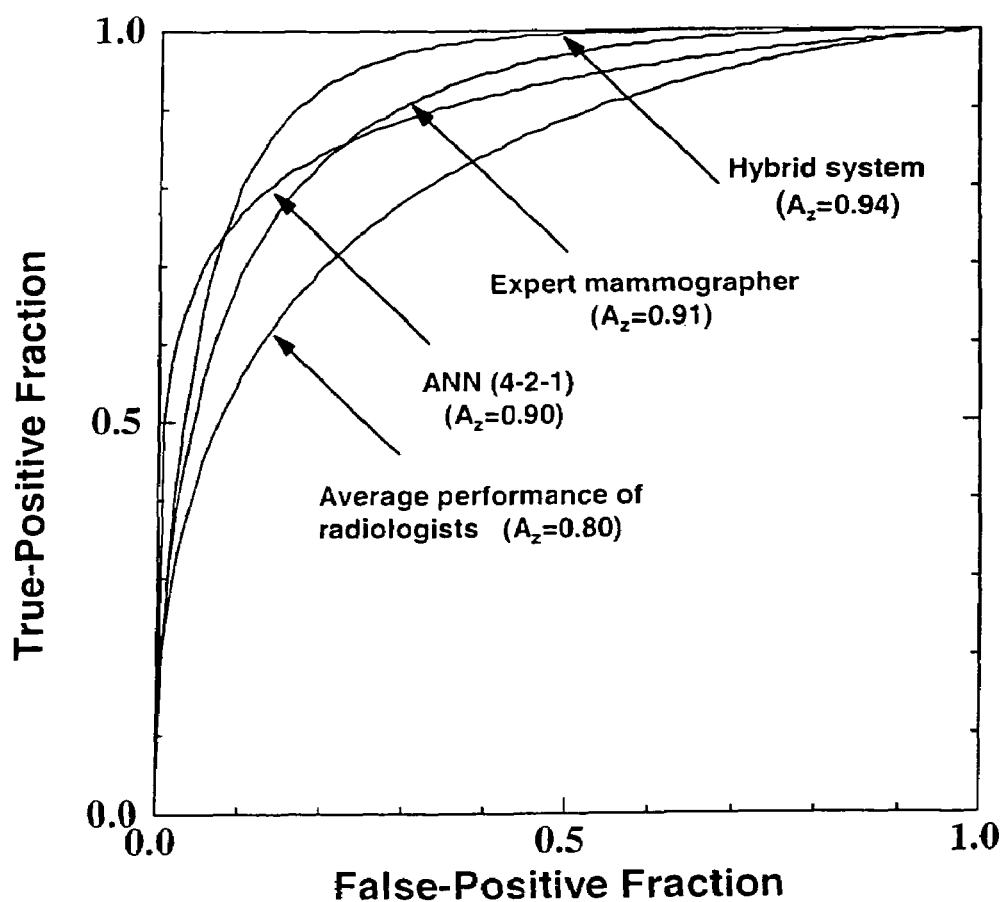
FIG. 5 is a graph illustrating the performance in terms of an ROC curve of the computer analysis on the database used as the reference database in the intelligent search workstation, wherein the performance is given for the task of distinguishing malignant from benign lesions.

The method is initially trained with 95 mammograms containing masses from 65 patients. Features related to the margin, shape, and density of each mass are extracted automatically from the image data and merged into an estimate of the likelihood of malignancy using artificial neural networks. These features include a spiculation measure, a radial gradient index, and two density measures. The round-robin performance of the computer in distinguishing between benign and malignant masses is evaluated by receiver operating characteristic (ROC) analysis. As shown in FIG. 5, the computer classification scheme based on the hybrid system yielded an $A_z$ value of 0.94, similar to that of an experienced mammographer ($A_z$=0.91) and the computer classification scheme based on the ANN system ($A_z$=0.90) and statistically significantly higher than the average performance of five radiologists with less mammographic experience ($A_z$=0.80). With the database used, the computer scheme achieved, at 100% sensitivity, a positive predictive value of 83%, which is 12% higher than that of the experienced mammographer and 21% higher than that of the average performance of the less experienced mammographers at a p-value of less than 0.001.

The computerized mass classification method is next independently evaluated on a 110-case clinical database consisting of 50 malignant and 60 benign cases. The effects of variations in both case mix and in film digitization technique on the performance of the method are assessed. Categorization of lesions as malignant or benign using the computer achieved an $A_z$ value (area under the ROC curve) of 0.90 on the prior training database (i.e., Fuji scanner digitization) in a round-robin evaluation, and $A_z$ values of 0.82 and 0.81 on the independent database for Konica and Lumisys digitization formats, respectively. However, the statistical comparison of these performances failed to show a statistical significant difference between the performance on the training database and that on the independent validation database (p-values>0.10). Thus, the present computer-based method for the classification of lesions on mammograms is shown to be robust to variations in case mix and film digitization technique.

Figure 6:
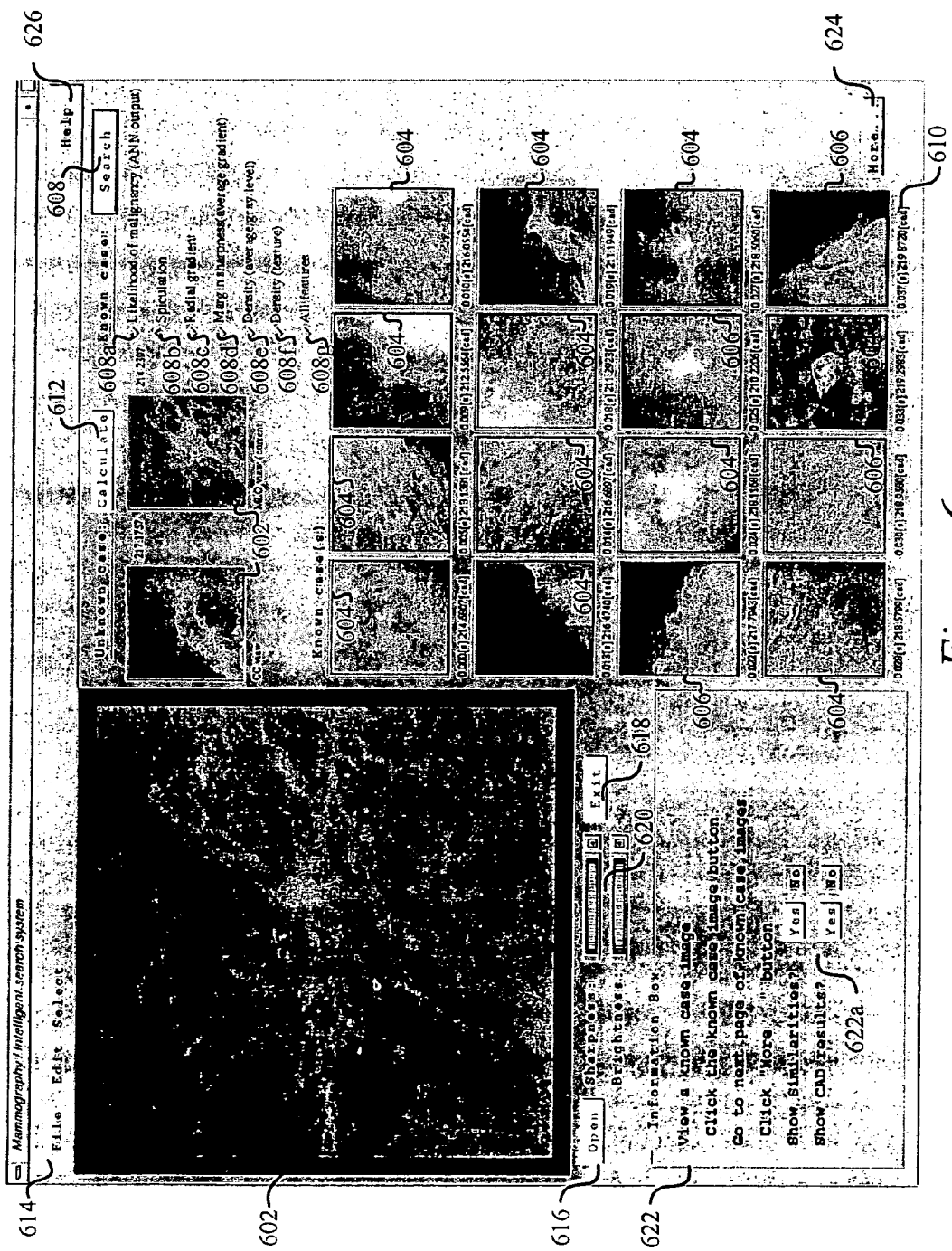
FIG. 6 is an image illustrating an example of the workstation interface for an unknown case using a color display where red indicates a malignant case and green indicates a benign case for a malignant case.

Integration of Automated Mass Lesion Classification into the Intelligent Workstation The output of the automated classification method (FIG. 4, step 416) is used to intelligently search for similar lesions in the known database (FIG. 4, step 418 and FIG. 1 step 114). FIG. 6 shows an example of the workstation graphical user interface (GUI) for an unknown case 602 using, for example, a color display where a red border 604 indicates a malignant case and green border 606 indicates a benign case for a case deemed malignant by the computer scheme.

Figure 7:
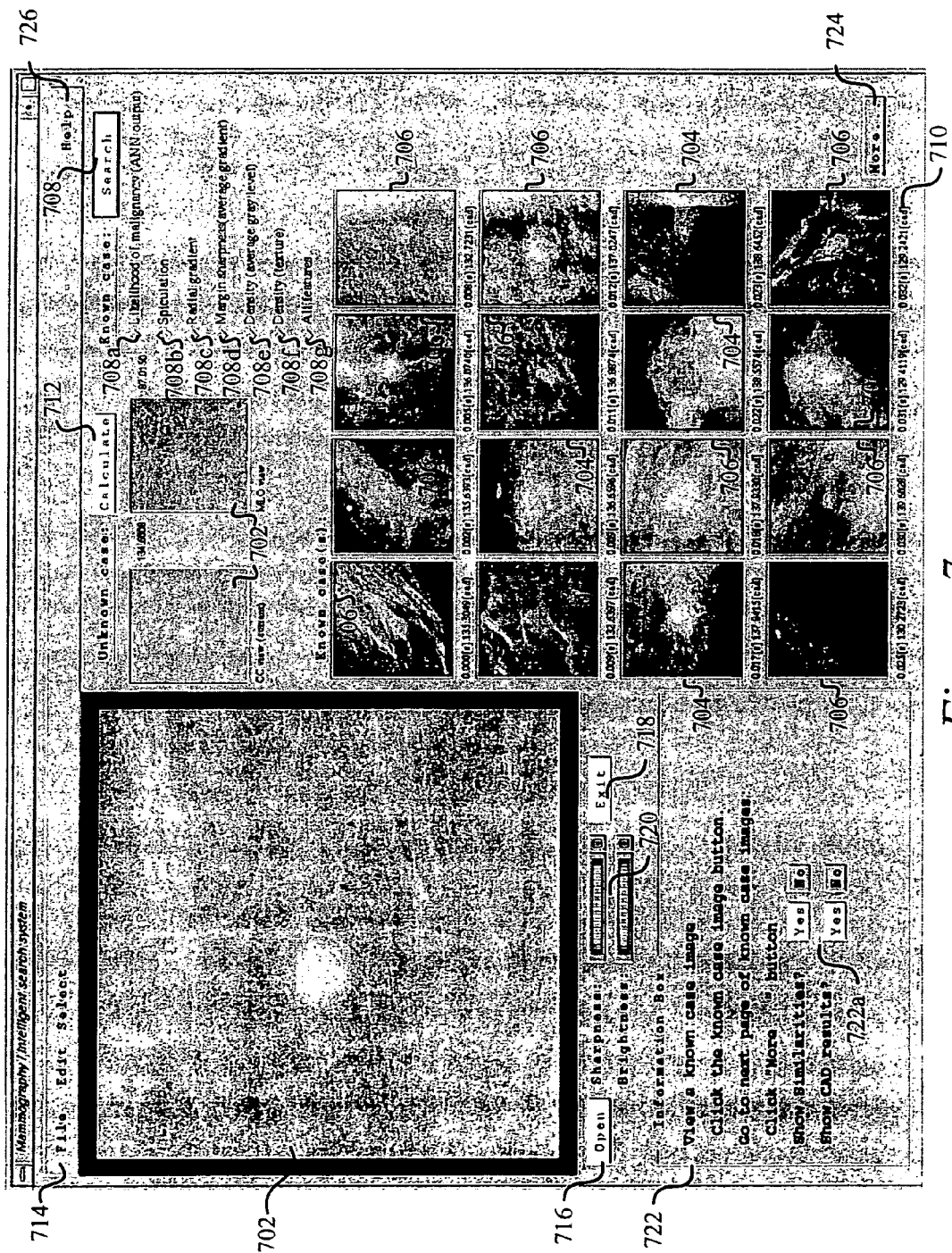
FIG. 7 is an image illustrating an example of the workstation interface for an unknown case using a color display where red indicates a malignant case and green indicates a benign case for a benign case.

FIG. 7 shows an example of the workstation GUI for an unknown case 702 using, for example, a color display where a red border 704 indicates a malignant case and a green border 706 indicates a benign case for a case deemed benign by the computer scheme. Similar displays can be given for black and white displays by, for example, outlining the known malignant lesions in black and outlining the known benign lesions in white.

Referring to FIGS. 6 and 7, the user specifies how the search 608/708 is to occur—either by a single feature, such as likelihood of malignancy 608a/708a, spiculation 608b/708b, radial gradient 608c/708c, margin sharpness 608d/708d, average gray level 608e/708e, texture 608f/708f, etc., by a combination of features (in which, e.g., the Euclidean distance is calculated for the combination of features between the unknown case and each of the known cases), or by all of the features 608g/708g. The display in the FIGS. 6 and 7, for example, is a search by spiculation and under each known case the Euclidean distance measure as well as the spiculation measure 610/710 is given. The user has the option to see the computer outputs, the similar known cases, or both.

The workstation interface shown in FIGS. 6 and 7 further includes a calculate button 612/712, file/edit/select drop down menus 614/714, an open button 616/716, an exit button 618/718, sharpness/brightness radio buttons 620/720, an information box 622/722 including yes/no buttons 622a/722a for showing similarities and CAD results, a display more images button 624/724 and a help drop down menu 626/726.

Figure 8:
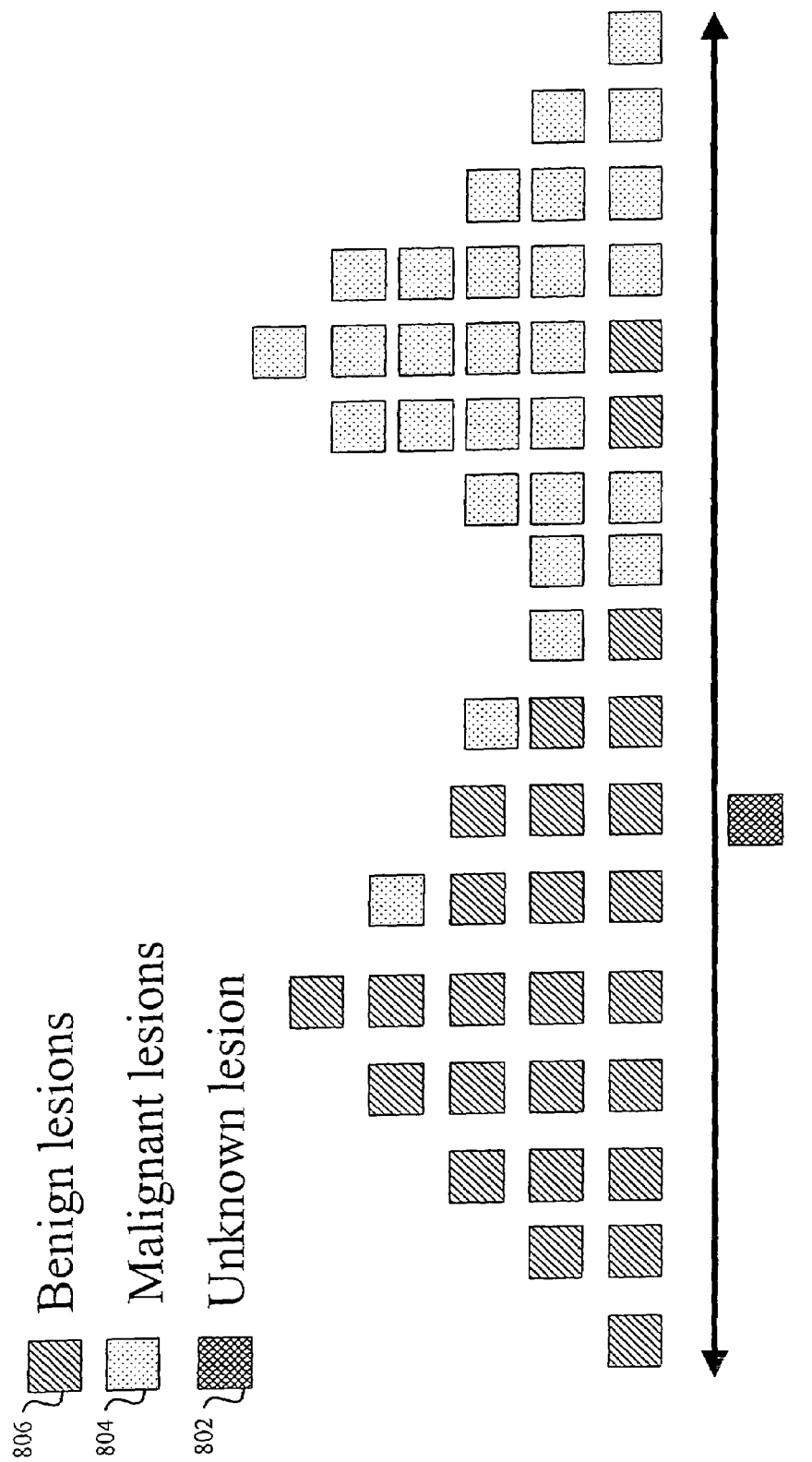
FIG. 8 is a diagram illustrating the placement of the unknown case on the probability distribution axes of the malignant and benign cases, wherein instead of just displaying typical malignant and benign cases that are similar, the computer display shows relative similarity of the malignant and benign known cases by use of a color-coding of the similar lesions, whereby the probability distributions of the malignant and benign cases in the known database are shown by images along with the "location" of the unknown case relative to the two distributions.

FIG. 8 further explains the search method by schematically showing the location of an unknown case 802 (e.g., which may be shown in blue) relative to the distribution of malignant 804 (e.g., which may be shown in red) and benign 806 (e.g., which may be shown in green) cases with respect to a given feature (and/or combination of features). The output of the cases can be in terms of those closest (in terms of absolute distance) as shown in FIGS. 6 and 7 or in terms of actual distance by not employing an absolute-type similarity index. For example, if only spiculation is chosen for searching, the unknown cases can be displayed with known cases on either side of it indicating which of the known cases are more spiculated and which ones are less spiculated.

Observer Study Results

At the Radiological Society of North America (RSNA) 2000, the inventors ran a demonstration of the intelligent search workstation of the present invention to show how it helps radiologists. The demo included 20 mammographic cases. For each case, the radiologists first saw the mammograms including the standard views of MLO, where MLO is medial-lateral oblique view (mammographic view of the breast at a side ways oblique angle) and CC, where CC is a cranial-caudal view (mammographic view of the breast from the head downwards), any special views of MLO and CC, as well as a 4 on 1 view showing the location of the lesion in the breast, where the 4 on 1 view is a collage of the left and right CC views on top of the left and right MLO views. Each radiologist was then asked to give his/her likelihood of malignancy on a scale from zero to 100, and also give his/her recommendation for either biopsy or follow-up. Then the computer output of the likelihood of malignancy was shown along with the resulting images from the intelligent search from the reference library. Each radiologist then was again asked for his/her likelihood of malignancy and recommendation. After 20 cases, the sensitivity and specificity was calculated based on their biopsy/follow-up recommendation, where:

Sensitivity is the percentage of malignant (i.e., cancerous) cases sent to biopsy. So a sensitivity of 0.92 is 92%. The higher the sensitivity the better.

Specificity is determined by subtracting the false-positive rate FPR, i.e., the number of benign cases sent to biopsy, from unity, i.e., (1-FPR). The higher the specificity, the better.

TABLE 1

RSNA 2000 Exhibit Observer Study Results on Mass Lesion Classification (Biopsy vs. Follow-Up)

| Reader Type | Number of Observers | Sensitivity (w/o CAD) | Sensitivity (w/ CAD) | Specificity (w/o CAD) | Specificity (w/ CAD) |
|---|---|---|---|---|---|
| Mammographers | 29 | 0.81 | 0.83 | 0.62 | 0.67 |
| Radiologist Non-Mammographers | 13 | 0.79 | 0.85 | 0.55 | 0.74 |

In Table 1 above, "with CAD" includes the computer output of the likelihood of malignancy and the results of intelligent search on a known atlas of images, using the intelligent search workstation of the present invention. From Table 1, one sees that both the sensitivity and the specificity increased for mammographers and for radiologists (who do not read mammograms regularly) using the intelligent search workstation of the present invention.

Figure 9:
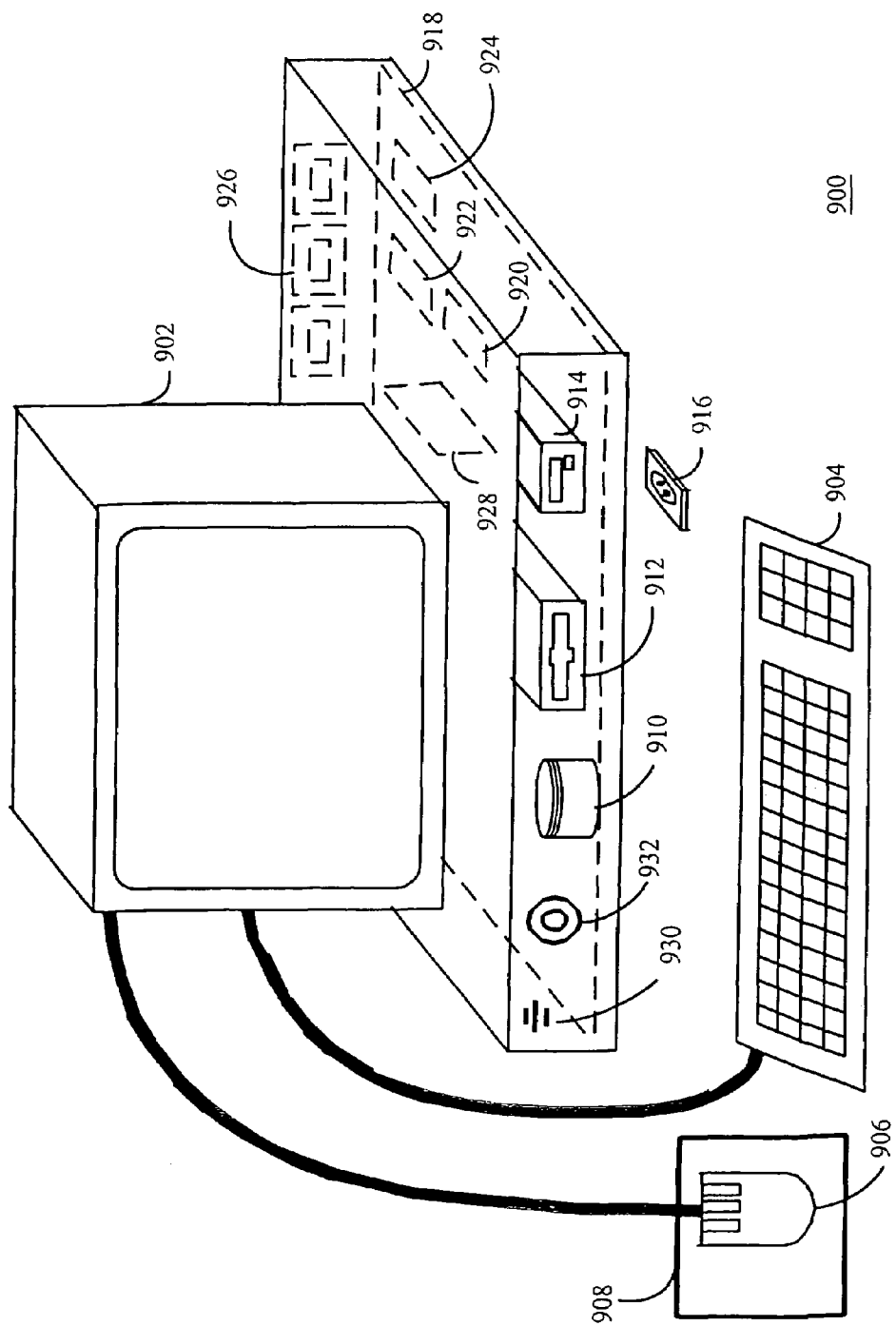
FIG. 9 is a schematic illustration of a general purpose computer which can be programmed according to the teachings of the present invention.

FIG. 9 is a schematic illustration of a general purpose computer 900 which can be programmed according to the teachings of the present invention. In FIG. 9, the computer 900 implements the processes of the present invention, wherein the computer includes, for example, a display device 902 (e.g., a touch screen monitor with a touch-screen interface, etc.), a keyboard 904, a pointing device 906, a mouse pad or digitizing pad 908, a hard disk 910, or other fixed, high density media drives, connected using an appropriate device bus (e.g., a SCSI bus, an Enhanced IDE bus, an Ultra DMA bus, a PCI bus, etc.), a floppy drive 912, a tape or CD ROM drive 914 with tape or CD media 916, or other removable media devices, such as magneto-optical media, etc., and a mother board 918. The mother board 918 includes, for example, a processor 920, a RAM 922, and a ROM 924 (e.g., DRAM, ROM, EPROM, EEPROM, SRAM, SDRAM, and Flash RAM, etc.), I/O ports 926 which may be used to couple to an image acquisition device and optional special purpose logic devices (e.g., ASICs, etc.) or configurable logic devices (e.g., GAL and re-programmable FPGA) 928 for performing specialized hardware/software functions, such as sound processing, image processing, signal processing, neural network processing, automated classification, etc., a microphone 930, and a speaker or speakers 932.

As stated above, the system includes at least one computer readable medium. Examples of computer readable media are compact discs, hard disks, floppy disks, tape, magneto-optical disks, PROMs (EPROM, EEPROM, Flash EPROM), DRAM, SRAM, SDRAM, etc. Stored on any one or on a combination of computer readable media, the present invention includes software for controlling both the hardware of the computer 900 and for enabling the computer 900 to interact with a human user. Such software may include, but is not limited to, device drivers, operating systems and user applications, such as development tools. Such computer readable media further includes the computer program product of the present invention for performing any of the processes according to the present invention, described above. The computer code devices of the present invention can be any interpreted or executable code mechanism, including but not limited to scripts, interpreters, dynamic link libraries, Java classes, and complete executable programs, etc.

The programming of general purpose computer 900 may include a software module for digitizing and storing images obtained from an image acquisition device. Alternatively, the present invention can also be implemented to process digital data derived from images obtained by other means, such as a picture archive communication system (PACS). In other words, often the digital images being processed will be in existence in digital form and need not be converted to digital form in practicing the invention.

Accordingly, the mechanisms and processes set forth in the present description may be implemented using a conventional general purpose microprocessor or computer programmed according to the teachings in the present specification, as will be appreciated by those skilled in the relevant art(s). Appropriate software coding can readily be prepared by skilled programmers based on the teachings of the present disclosure, as will also be apparent to those skilled in the relevant art(s). However, as will be readily apparent to those skilled in the art, the present invention also may be implemented by the preparation of application-specific integrated circuits or by interconnecting an appropriate network of conventional component circuits.

The present invention thus also includes a computer-based product which may be hosted on a storage medium and include instructions which can be used to program a general purpose microprocessor or computer to perform processes in accordance with the present invention. This storage medium can include, but is not limited to, any type of disk including floppy disks, optical disks, CD-ROMs, magneto-optical disks, ROMs, RAMs, EPROMs, EEPROMs, flash memory, magnetic or optical cards, or any type of media suitable for storing electronic instructions.

Recapitulating, the method, system and computer readable medium employs an intelligent search workstation for the computer assisted interpretation of medical images. The method, system and computer readable medium of the intelligent search interface takes as input an unknown medical image and searches through a set of cases with known diagnoses by way of a similarity index. The interface then displays images having similar features in a specified order. The search is directed by computer-extracted features (although it can easily be adapted for human-extracted features) and an estimate of the likelihood of the diagnosis of the unknown lesion is obtained with use of an artificial neural network (ANN, although others classifiers can be used). The similarity index is calculated using an Euclidean distance measure (although other measures of similarity can be employed). The displayed images can have their diagnostic truth displayed by means of enclosure by a green or red outline (for benign or malignant, respectively). In a sense, the display is showing the distribution of malignant and benign cases in the known database (or databank) that are similar to the unknown case. The significance of this method, system and computer readable medium is in the diagnosis of lesions and medical conditions, especially for confusing cases. The method, system and computer readable medium can also be used together with computerized output of the features and likelihood of malignancy (computer-aided diagnosis).

Although the present invention is described in terms of practicing the method on mammographic image data sets, the intelligent workstation can be implemented for other medical images, such as chest radiography, ultrasound, magnetic resonance imaging, etc., in which a computerized analysis of image or lesion features is performed with respect to some disease state, as will be appreciated by those skilled in the relevant art(s).

Numerous modifications and variations of the present invention are possible in light of the above teachings. It is therefore to be understood that within the scope of the appended claims, the invention may be practiced otherwise than as specifically described herein.

LIST OF REFERENCES

[1]. Huo Z, Giger M L, Vyborny C J, Bick U, Lu P, Wolverton D E, Schmidt R A: Analysis of spiculation in the computerized classification of mammographic masses" *Medical Physics* 22:1569–1579, 1995.

[2]. Huo Z, Giger M L, Vyborny C J, Wolverton D E, Schmidt R A, Doi K: Automated computerized classification of malignant and benign mass lesions on digitized mammograms. *Academic Radiology* 5: 155–168, 1998.

[3]. Huo Z, Giger M L, Metz C E: Effect of dominant features on neural network performance in the classification of mammographic lesions. *PMB* 44: 2579–2595, 1999.

[4]. Swett H A, Fisher P R, Cohn A I, et al: Expert system controlled image display. *Radiology* 172:487, 1989

[5]. Swett H A, Miller P A. ICON: a computer-based approach to differential diagnosis in radiology. *Radiology* 163:555, 1987

[6]. Sklansky J, Taso E Y, Ornes C, Disher A C. A visualized mammographic database in computer-aided diagnosis. *Computer-Aided Diagnosis in Medical Imaging*. Eds Doi K, MacMahon, Giger M L, Hoffmann K R. Pp. 215–220. Elsevier Science, 1999.

What is claimed as new and desired to be secured by Letters Patent of the United States is:

1. In a user interface of a computer-aided detection (CAD) system, a method for facilitating user diagnosis of a detected lesion in an x-ray mammogram, comprising:
    displaying a first image of the detected lesion to the user;
    selecting a plurality of reference images from a reference lesion database based on similarity to said detected lesion with respect to at least one computed feature characteristic; and
    displaying said plurality of reference images near the first image, each reference image comprising a lesion with a known diagnosis and being visibly marked according to said known diagnosis.

2. The method of claim 1, comprising:
    displaying said reference images sized smaller than said first image and simultaneously with display of said first image.

3. The method of claim 2, wherein said at least one computed feature characteristic comprises:
    a likelihood-of-malignancy metric computed by the CAD system.

4. The method of claim 2, wherein said at least one computed feature characteristic is selected from the group consisting of:
    a margin sharpness metric; a spiculation metric; a mass density metric; and a likelihood-of-malignancy metric computed by the CAD system.

5. The method of claim 2, comprising:
    spatially ordering said reference images on said user interface according to said computed feature characteristic.

6. The method of claim 1, wherein the detected lesion is a CAD-detected lesion selected by the user from a CAD-annotated x-ray mammogram display.

7. In a user interface of a computer-aided detection (CAD) system, a method for facilitating user diagnosis of a detected lesion in an x-ray mammogram, comprising:
    receiving a selection of the detected lesion on a first display;
    displaying a first image of the detected lesion on a second display; and
    displaying a plurality of reference images on the second display near the first image, each reference image based on a similarity to said detected lesion with respect to at least one computed feature characteristic and comprising a lesion with a known diagnosis and being visibly marked according to said known diagnosis, including displaying said reference images sized smaller than said first image and simultaneously with display of said first image on said second display.

8. The method of claim 7, comprising:
    selecting said plurality of reference images from a reference lesion database based on similarity to said detected lesion with respect to at least one computed feature characteristic.

9. The method of claim 8, wherein said at least one computed feature characteristic comprises:
    a likelihood-of-malignancy metric computed by the CAD system.

10. The method of claim 8, wherein said at least one computed feature characteristic is selected from the group consisting of a margin sharpness metric, a spiculation metric, a mass density metric, and a likelihood-of-malignancy metric computed by the CAD system.

11. The method of claim 8, comprising:
    spatially ordering said reference images on said user interface according to said computed feature characteristic.

12. In a user interface of a computer-aided detection (CAD) system, a method for facilitating user diagnosis of a detected lesion in an x-ray mammogram, comprising:
    displaying a first image of the detected lesion to the user;
    displaying a plurality of reference images near the first image, each reference image based on a similarity to said detected lesion with respect to at least one computed feature characteristic and comprising a lesion with a known diagnosis and being visibly marked according to said known diagnosis, including spatially ordering said reference images on said user interface according to a degree of similarity with said detected lesion with respect to at least one computed feature characteristic.

13. The method of claim 12, wherein said at least one computed feature characteristic comprises:
    a likelihood-of-malignancy metric computed by the CAD system.

14. The method of claim 12, wherein said at least one computed feature characteristic is selected from the group consisting of a margin sharpness metric, a spiculation metric, a mass density metric, and a likelihood-of-malignancy metric computed by the CAD system.

15. The method of claim 12, comprising displaying said reference images sized smaller than said first image and simultaneously with display of said first image.

* * * * *

UNITED STATES PATENT AND TRADEMARK OFFICE
CERTIFICATE OF CORRECTION

| | | |
|---|---|---|
| PATENT NO. | : 7,184,582 B2 | Page 1 of 1 |
| APPLICATION NO. | : 10/793799 | |
| DATED | : February 27, 2007 | |
| INVENTOR(S) | : Maryellen L. Giger et al. | |

It is certified that error appears in the above-identified patent and that said Letters Patent is hereby corrected as shown below:

Column 1, line 6: insert, --This nvention was made with government support under DAMD 17-96-1-6058 awarded by The United States Army. The government has certain rights in the invention-- .

Signed and Sealed this

Seventh Day of August, 2007

JON W. DUDAS
*Director of the United States Patent and Trademark Office*